US008926548B2

(12) United States Patent
Fujita et al.

(10) Patent No.: US 8,926,548 B2
(45) Date of Patent: Jan. 6, 2015

(54) AGENT FOR PREVENTING BLEEDING FROM CEREBRAL CORTICAL VEIN

(75) Inventors: Yasutaka Fujita, Naruto (JP); Kazuhisa Doi, Naruto (JP); Shuji Kamikawa, Tokyo (JP)

(73) Assignee: Otsuka Pharmaceutical Factory, Inc., Naruto-shi (JP)

( * ) Notice: Subject to any disclaimer, the term of this patent is extended or adjusted under 35 U.S.C. 154(b) by 365 days.

(21) Appl. No.: 12/526,322

(22) PCT Filed: Feb. 5, 2008

(86) PCT No.: PCT/JP2008/051804
§ 371 (c)(1),
(2), (4) Date: Jan. 20, 2010

(87) PCT Pub. No.: WO2008/096722
PCT Pub. Date: Aug. 14, 2008

(65) Prior Publication Data
US 2010/0178363 A1     Jul. 15, 2010

(30) Foreign Application Priority Data
Feb. 8, 2007   (JP) ................................. 2007-028975

(51) Int. Cl.
| A61K 33/06 | (2006.01) |
| A61P 7/00 | (2006.01) |
| A61K 31/7004 | (2006.01) |
| A61K 31/19 | (2006.01) |
| A61K 33/00 | (2006.01) |
| A61K 33/10 | (2006.01) |
| A61K 33/14 | (2006.01) |

(52) U.S. Cl.
CPC .............. *A61K 31/7004* (2013.01); *A61K 31/19* (2013.01); *A61K 33/00* (2013.01); *A61K 33/10* (2013.01); *A61K 33/14* (2013.01)
USPC .............................................. 604/19; 604/28

(58) Field of Classification Search
USPC .......................................................... 514/46
See application file for complete search history.

(56) References Cited

U.S. PATENT DOCUMENTS

| 2,751,326 | A | * | 6/1956 | Hajdu et al. | .................. | 424/9.2 |
| 6,232,128 | B1 | | 5/2001 | Iguchi et al. | | |
| 6,764,481 | B1 | | 7/2004 | Inada et al. | | |
| 7,047,708 | B2 | | 5/2006 | Inada et al. | | |
| 2003/0045608 | A1 | | 3/2003 | Ochiai et al. | | |
| 2006/0057065 | A1 | | 3/2006 | Wang | | |
| 2006/0057067 | A1 | | 3/2006 | Wang | | |
| 2006/0073098 | A1 | | 4/2006 | Wang | | |
| 2006/0128798 | A1 | | 6/2006 | Wang | | |

FOREIGN PATENT DOCUMENTS

| JP | 63-20550 | B2 | 4/1988 |
| JP | 63-17474 | Y2 | 5/1988 |
| JP | 63-309263 | A | 12/1988 |
| JP | 02-004671 | A | 1/1990 |
| JP | 5-8318 | A | 1/1993 |
| JP | 11-197215 | A | 7/1999 |
| JP | 11-276547 | A | 10/1999 |
| JP | 2002-173422 | A | 6/2002 |
| JP | 2002-234102 | A | 8/2002 |
| JP | 2003-267451 | A | 9/2003 |
| JP | 3112358 | U | 8/2005 |
| JP | 2005-349182 | A | 12/2005 |
| WO | 97/48365 | A1 | 12/1997 |
| WO | 01/44385 | A1 | 6/2001 |
| WO | 2006-115057 | A1 | 11/2006 |

OTHER PUBLICATIONS

Sasaki et al., "Urokinase Cisteranl Irrigation Therapy for Prevention of Symtomatic Vasospasm After Aneurysmal Subarachnoid Hemorrhage: A Study of Urokinase Concentration and the Fibrinolytic System." Stroke, Jun. 2000:31;1256-1262.*

CDM Lavoisier, "Lavoisier Ringer Lacatate, solution for infusion." Product Information, dated Feb. 1998.*

Tsugio Yanagihashi et al.; Relationship between Chemical Constituents in Drinking Water and Morality rates from Cerebro-Cardio-Vascular Diseases in Kagoshima Prefecture Minzoku Eisei, 1989, vol. 55, No. 5, pp. 244 to 252. Cited in ISR.

Hiroshi Komachi; "Infusion Therapy for Patients with Disturbance of Consciousness or Cerebrovascular Disease"; Advances of Medical Science, Jan. 29, 1994, vol. 168, No. 5, pp. 397 to 400. Translation of Document cited on IDS filed Nov. 5, 2009.

International Preliminary Report on Patentability issued in International Patent Application No. PCT/JP2008/051804, dated Aug. 11, 2009.

Writtten Opinion of the International Searching Authority issued in International Patent Application No. PCT/JP2008/051804, dated Mar. 11, 2008.

(Continued)

*Primary Examiner* — Walter Webb
(74) *Attorney, Agent, or Firm* — Westerman, Hattori, Daniels & Adrian, LLP

(57) ABSTRACT

The present invention provides: a superficial cerebral vascular bleeding inhibitor comprising an aqueous solution containing 120 to 160 mEq/L of sodium ion, 1 to 5 mEq/L of calcium ion, and 75 to 165 mEq/L of chloride ion; the superficial cerebral vascular bleeding inhibitor further comprising 1 to 5 mEq/L of potassium ion; and a packaged container containing the superficial cerebral vascular bleeding inhibitor (with or without potassium ion).

The superficial cerebral vascular bleeding inhibitor of the present invention can effectively prevent or inhibit bleeding from superficial cerebral blood vessels in the field of neurosurgery such as intracranial surgery and the like, thereby capable of securing a clear operating field during intracranial surgery and inhibiting the occurrence of post-surgery damage.

2 Claims, 1 Drawing Sheet

(56) References Cited

OTHER PUBLICATIONS

International Search Report issued in International Patent Application No. PCT/JP2008/051804, dated Mar. 11, 2008.

Uchida, K., et al., "Possible harmful effects on central nervous system cells in the use of physiological saline as an irrigant during neurosurgical procedures", Surgical Neurology, vol. 62, No. 2, Aug. 1, 2004, pp. 96-105; cited in Extended European Search Report dated May 21, 2014, issued in European Patent Application No. 08704431.9.

Doi, K. et al.,"Various irrigation fluids affect postoperative brain edema and cellular damage during experimental neurosurgery in rats", Surgical Neurology, vol. 66, No. 6, Dec. 1, 2006, pp. 565-571; cited in Extended European Search Report dated May 21, 2014, issued in European Patent Application No. 08704431.9.

Extended European Search Report dated May 21, 2014, Issued in European Patent Application No. 08704431.9 (7 pages).

* cited by examiner

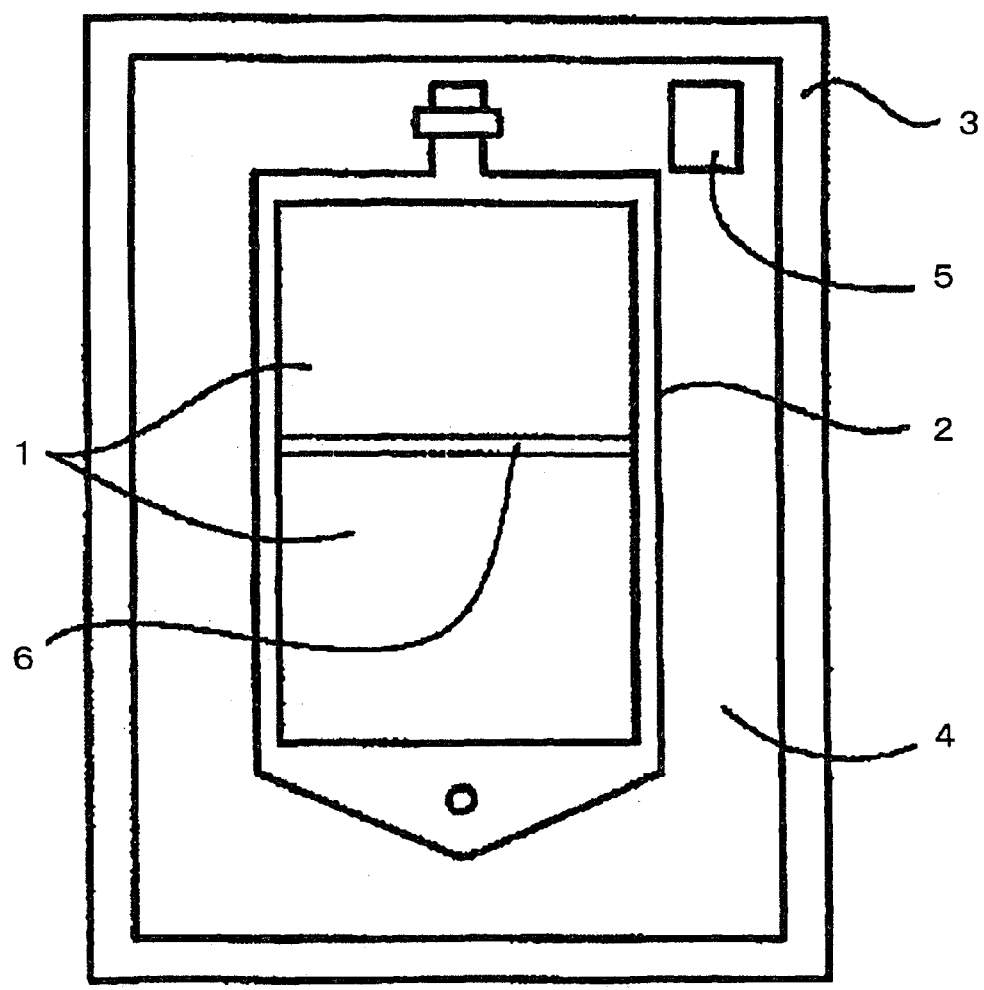

AGENT FOR PREVENTING BLEEDING FROM CEREBRAL CORTICAL VEIN

TECHNICAL FIELD

The present invention relates to a superficial cerebral vascular bleeding inhibitor having an effect of inhibiting bleeding from superficial cerebral blood vessels during intracranial surgery and the like in the field of neurosurgery, and to a packaged container containing the superficial cerebral vascular bleeding inhibitor.

BACKGROUND ART

Removal of tissues in brain tumor removal surgery and the like is usually accompanied by bleeding. Physiologically, such bleeding in the surgical site ceases due to blood coagulation and/or vasoconstriction. When such bleeding continues, a hemostatic procedure is carried out using electrocauterization, oxidized cellulose, gelatin sponge, fibrin glue, etc.

When bleeding continues during surgery, it may not only obscure the operating field but also may further cause inflammatory damage to brain cells. Thus, physiological hemostasis in a larger number of bleeding sites at an early state is believed to have a great clinical significance.

Physiological saline solution, Ringer's lactate solution, and the like are used during surgery in the neurosurgical field, as an irrigation fluid to prevent dehydration of brain cells, wash out blood, and the like. In addition, various artificial cerebrospinal fluids have been proposed in order to alleviate side-effects such as convulsion, headache, fever, etc., which are problems associated with the use of physiological saline solution as an irrigation or perfusion fluid. A ventricular irrigation fluid capable of protecting brain tissues during surgery has also been reported (see Patent Document 1 and the like below). Further, in the neurosurgical field, there has been reported an artificial cerebrospinal fluid capable of reducing or preventing cerebral edema that may occur when an artificial cerebrospinal fluid is used as an irrigation or perfusion fluid (see Patent Document 2 below).

However, the effects of irrigation fluids on the hemostasis process are not known, and a superficial cerebral vascular bleeding inhibitor that can effectively prevent or inhibit bleeding from superficial cerebral blood vessels has not been reported.

Because of the present situation described above, effectively preventing or inhibiting bleeding from superficial cerebral blood vessels to secure a clear operating field is a very important object in the neurosurgical field.

CITATION LIST

Patent Literature

[PTL 1] Japanese Unexamined Patent Publication No. 2002-173422
[PTL 2] International Publication WO 2006/115057

SUMMARY OF INVENTION

Technical Problem

The present invention was conceived in view of the above-described current situation of the conventional technology. A main object of the present invention is to provide a superficial cerebral vascular bleeding inhibitor capable of securing an operating field during surgery and inhibiting the occurrence of post-surgery damage by effectively preventing or inhibiting bleeding from superficial cerebral blood vessels during intracranial surgery and the like in the field of neurosurgery.

Solution to Problem

The present inventors, conducted extensive research to achieve the above object. As a result, they have made the following discoveries: when an aqueous solution containing a predetermined amount of specific electrolytic ions as shown below, and further containing, as necessary, at least one ion selected from the group consisting of lactate ion, acetate ion, and bicarbonate ion is used for irrigation or perfusion of the surgical site during intracranial surgery, an entirely new effect of preventing or inhibiting bleeding from superficial cerebral blood vessels is produced. The present invention is accomplished based on this finding.

Specifically, the present invention provides the following superficial cerebral vascular bleeding inhibitor and a packaged container containing the superficial cerebral vascular bleeding inhibitor.

1: A superficial cerebral vascular bleeding inhibitor, comprising an aqueous solution containing electrolyte ions in the following ranges:
   120 to 160 mEq/L of sodium ion,
   1 to 5 mEq/L of calcium ion, and
   75 to 165 mEq/L of chloride ion.
2. The superficial cerebral vascular bleeding inhibitor of Item 1, further comprising 1 to 5 mEq/L of potassium ion.
3. The superficial cerebral vascular bleeding inhibitor of Item 2, wherein the potassium ion concentration and the calcium ion concentration are in the following ranges:
   2.5 to 4.5 mEq/L of potassium ion, and
   2.0 to 3.5 mEq/L of calcium ion.
4. The superficial cerebral vascular bleeding inhibitor of Item 1, further comprising at least one ion selected from the group consisting of lactate ion, acetate ion, and bicarbonate ion, in the range of 5 to 45 mEq/L.
5. The superficial cerebral vascular bleeding inhibitor of Item 2, further comprising at least one ion selected from the group consisting of lactate ion, acetate ion, and bicarbonate ion, in the range of 5 to 45 mEq/L.
6. A packaged container containing the superficial cerebral vascular bleeding inhibitor containing a bicarbonate ion of Item 4, wherein the container is a gas-permeable plastic container having at least two intercommunicable chambers therein, the bicarbonate ion and the calcium ion are each separately contained in the chambers of the container, the container is packaged with a gas-barrier packaging member, and a carbon dioxide atmosphere is established in a space between the container and the packaging member.
7. A packaged container containing the superficial cerebral vascular bleeding inhibitor containing a bicarbonate ion of Item 5, wherein the container is a gas-permeable plastic container having at least two intercommunicable chambers therein, the bicarbonate ion and the calcium ion are each separately contained in the chambers of the container, the container is packaged with a gas-barrier packaging member, and a carbon dioxide atmosphere is established in a space between the container and the packaging member.
8. The packaged container of Item 6, wherein the container further contains a reducing sugar in a chamber different from the chamber containing the bicarbonate ion.
9. The packaged container of Item 7, wherein the container further contains a reducing sugar in a chamber different from the chamber containing the bicarbonate ion.

10. The packaged container of Item 6, further comprising a pH-indicating device in a space between the container and the packaging member, wherein the pH-indicating device detects the concentration of carbon dioxide in the space and undergoes a change in color in accordance with a change in the concentration.
11. The packaged container of Item 7, further comprising a pH-indicating device in a space between the container and the packaging member, wherein the pH-indicating device detects the concentration of carbon dioxide in the space and undergoes a change in color in accordance with a change in the concentration.

A superficial cerebral vascular bleeding inhibitor of the present invention and a packaged container containing the superficial cerebral vascular bleeding inhibitor are described in detail below.

(1) Superficial Cerebral Vascular Bleeding Inhibitor

The superficial cerebral vascular bleeding inhibitor of the present invention comprises an aqueous solution containing electrolyte ions in the following ranges:

| | |
|---|---|
| sodium ion | 120 to 160 mEq/L, |
| calcium ion | 1 to 5 mEq/L, and |
| chloride ion | 75 to 165 mEq/L. |

When the aqueous solution having the specific composition as described above is used for intracranial irrigation or perfusion in intracranial surgery, bleeding from superficial cerebral blood vessels during surgery can be effectively prevented or inhibited. As a result, a clear operating field can be secured during intracranial surgery and the occurrence of post-surgery damage can be inhibited. It is a completely novel finding that such effects can be attained by the use of an aqueous solution having the above specific composition.

It is preferable that the superficial cerebral vascular bleeding inhibitor of the present invention further contains 1 to 5 mEq/L of potassium ion.

It is particularly preferable that the potassium ion concentration is 2.5 to 4.5 mEq/L and the calcium ion concentration is 2.0 to 3.5 mEq/L in the superficial cerebral vascular bleeding inhibitor of the present invention. When the potassium ion concentration and the calcium ion concentration are in the above-described ranges, a particularly superior bleeding-inhibiting effect can be demonstrated.

The superficial cerebral vascular bleeding inhibitor of the present invention may further contain, as necessary, at least one ion selected from the group consisting of a lactate ion, acetate ion, and bicarbonate ion. A further superior bleeding-inhibiting effect can be demonstrated as a result of these ions being contained. Only one ion may be contained or two or more ions may be contained simultaneously. The concentration of at least one ion selected from the group consisting of lactate ion, acetate ion, and bicarbonate ion is preferably about 5 to about 45 mEq/L.

The superficial cerebral vascular bleeding inhibitor of the present invention may further contain a reducing sugar, a phosphoric acid, a magnesium ion, etc. Among the components, it is considered that the reducing sugar, phosphoric acid, magnesium ion, etc., are effective in maintaining or adjusting the electrical activity of brain neurons; the reducing sugar is also useful as an energy source for cells; and the phosphoric acid, calcium ion and magnesium ion are useful for cell energy metabolism. It is further considered that the magnesium ion is an effective ion for the activation of various intracellular enzymes. The use of the superficial cerebral vascular bleeding inhibitor of the present invention in a method of irrigation or perfusion during intracranial surgery can produce the above-described effects as well as the bleeding-inhibiting effect.

It is preferable that the reducing sugar be contained in the amount of about 0.1 to about 10 g/L, the phosphoric acid be contained in the amount of about 0.1 to about 5 mmol/L, and the magnesium ion be contained in the amount of about 0.5 to about 5 mEq/L to produce these effects.

A preferable example of the amount of each component in the superficial cerebral vascular bleeding inhibitor of the present invention is as follows:

| | |
|---|---|
| sodium ion | 120 to 160 mEq/L, |
| potassium ion | 1 to 5 mEq/L, |
| calcium ion | 1 to 5 mEq/L, |
| magnesium ion | 1 to 5 mEq/L |
| chloride ion | 75 to 155 mEq/L, | at least one ion selected from the group consisting of lactate ion, acetate ion, and bicarbonate ion

| | |
|---|---|
| phosphoric acid | 5 to 45 mEq/L |
| reducing sugar | 0 to 5 mmol/L, and |
| | 0 to 10 g/L. |

Further, a more preferable example of the amount of each component in the bleeding inhibitor of the present invention is as follows:

| | |
|---|---|
| sodium ion | 130 to 160 mEq/L, |
| potassium ion | 2.5 to 4.5 mEq/L, |
| calcium ion | 2.0 to 3.5 mEq/L, |
| magnesium ion | 1 to 4 mEq/L |
| chloride ion | 100 to 150 mEq/L, | at least one ion selected from the group consisting of lactate ion, acetate ion, and bicarbonate ion

| | |
|---|---|
| phosphoric acid | 10 to 40 mEq/L |
| reducing sugar | 0 to 3 mmol/L, and |
| | 0 to 5 g/L. |

The following are examples of sources for these electrolyte ions (compounds for providing electrolyte ions). More specifically, examples of sodium ion sources include sodium chloride, sodium acetate, sodium citrate, sodium dihydrogenphosphate, disodium hydrogenphosphate, sodium sulfate, sodium lactate, etc.; examples of potassium ion sources include potassium chloride, potassium acetate, potassium citrate, potassium dihydrogenphosphate, dipotassium hydrogenphosphate, potassium glycerophosphate, potassium sulfate, potassium lactate, etc.; examples of calcium ion sources include calcium chloride, calcium gluconate, calcium pantothenate, calcium lactate, calcium acetate, etc.; examples of magnesium ion sources include magnesium sulfate, magnesium chloride, magnesium acetate, etc.; examples of chloride ion sources include sodium chloride, potassium chloride, calcium chloride, magnesium chloride, etc. Sodium bicarbonate (sodium hydrogencarbonate) can be typically used as a bicarbonate ion source, however, sodium carbonate can also be used as the source. As a phosphoric acid source, not only phosphoric acid ($H_3PO_4$) itself but a salt thereof, for example, monopotassium phosphate, dipotassium phosphate, monosodium phosphate, disodium phosphate, etc., can also be used.

Glucose, maltose, etc. are used as reducing sugars. Usable as such electrolytic-ion-providing compounds, phosphoric acids, and reducing sugars are commercial products which can be easily obtained, and preferably products listed in Japanese Pharmacopoeia Reference Standards.

The compounds used as the above-described electrolytic ion sources are typically used in the anhydride form (NaCl, KCl, $NaHCO_3$, $CaCl_2$, $MgCl_2$, etc.), but are not limited thereto, and can also be used in a form containing water of crystallization i.e., hydrate, such as $CaCl_2.2H_2O$, $MgCl_2.6H_2O$, $MgSO_4.7H_2O$, etc. The amount by weight of each hydrate in the bleeding inhibitor of the present invention is different from that of anhydride; however, the amount may suitably be determined, regardless of the form, so that each electrolyte ion concentration in the bleeding inhibitor obtained by mixing these sources is within the range described above.

The bleeding inhibitor of the present invention is produced by dissolving the above components in water. The water to be used for the preparation of the bleeding inhibitor may be purified water (ion-exchanged water, reverse osmosis water, etc.), distilled water, etc. The water is preferably disinfected or sterilized.

The bleeding inhibitor of the present invention having the composition described above typically has a pH of from about 6.8 to about 8.2, more preferably from about 7 to about 7.5, and can be used as a bleeding inhibitor as is. If necessary, the pH can be further adjusted using a suitable pH-adjusting agent, for example, acids such as hydrochloric acid and alkalis such as sodium hydroxide.

The bleeding inhibitor of the present invention may further suitably contain, as necessary, other electrolytic components such as potassium acetate, calcium gluconate, etc.; other saccharides such as maltose, xylitol, trehalose, etc.; other components such as trace metals including copper, zinc, etc.; pharmaceutical components such as carnitine, etc. Furthermore, the bleeding inhibitor of the present invention can contain thrombolytic agents such as glutathione, ketone bodies, urokinase, etc.; antibiotics such as gentamicin sulfate, amikacin sulfate, etc.; anticancer agents such as methotrexate (MTX), etc.; pharmaceutical components such as ascorbic acid, etc.

(2) Packaged Container Containing the Superficial Cerebral Vascular Bleeding Inhibitor of the Present Invention The superficial cerebral vascular bleeding inhibitor of the present invention having the above composition may be used as a single aqueous solution that simultaneously contains all the components. Alternatively, the superficial cerebral vascular bleeding inhibitor may be divided into at least two portions, contained in separate containers, and the internal fluid in each container may be mixed for use.

Particularly when the bleeding inhibitor of the present invention contains bicarbonate ion, the bicarbonate ion partially decomposes during the course of sterilization and storage of the fluid, and releases carbon dioxide gas, thereby disadvantageously causing a decomposition loss and a rise in the pH of the fluid. Therefore, the preferable embodiment of the product containing the bleeding inhibitor of the present invention is that which is able to avoid carbon dioxide gas generation and prevent a rise in the pH of the fluid.

An example of the preferable product embodiment (embodiment for enclosing the container) for the bleeding inhibitor of the present invention is a packaged container in which a gas-permeable plastic container having at least two inter-communicable chambers is packaged with a gas-barrier packaging member, with a carbon dioxide atmosphere established in a space between the container and the packaging member.

In such an embodiment of the packaged multiple-chamber container having at least two chambers, a solution containing bicarbonate ion (Solution A) is, for example, contained in a chamber (Chamber A) of the above container, an electrolyte solution containing calcium ion and, if necessary, magnesium ion (Solution B) is contained in another chamber (Chamber B), and a reducing sugar added as necessary is further contained in the chamber containing the above electrolyte solution (Solution B), or in a third chamber (Chamber C) separate from the foregoing two chambers. The solutions in the chambers are mixed at the time of use to attain the composition of the bleeding inhibitor of the present invention. A phosphoric acid added as necessary may preferably be contained simultaneously, for example, in the chamber containing the bicarbonate ion.

The concentration of each component and volume ratio in the internal chamber solutions are not limited insofar as the fluid prepared by mixing the solutions consequently has the above composition. A representative method for preparing the above form is as follows: sodium bicarbonate is dissolved in water for injection to prepare Solution A into which sodium chloride and/or potassium chloride may further be dissolved; calcium chloride, magnesium chloride, and, if necessary, a reducing sugar are dissolved in water for injection to prepare Solution B into which sodium chloride and/or potassium chloride may further be dissolved. Subsequently, the internal chamber solutions thus obtained are filtered using, for example, a membrane filter having a pore size of 0.45 µm, and contained in each chamber of the above-described gas-permeable plastic container. Chloride ion may be present in Solution A and/or Solution B.

When using the above packaged multiple-chamber container having at least two chambers, the occurrence of precipitation due to the formation of a bicarbonate that is highly insoluble from calcium ion and/or magnesium ion and bicarbonate ion can be prevented by placing the bicarbonate ion-containing solution in a chamber separate from the chamber where the calcium ion and/or magnesium ion are contained.

The above gas-permeable plastic container having at least two chambers may be any known one. Specific examples thereof include those equipped with closure means for a communicable part between two chambers (Japanese Examined Patent Publication No. 63-20550 and Japanese Examined Utility Model Publication No. 63-17474), those in which a sealing part zoning two chambers is easily communicable by pressing (Japanese Unexamined Patent Publications Nos. 63-309263 and 02-4671), etc. Examples of materials for the above container include various materials typically used for medical containers such as polyethylene, polypropylene, polyvinyl chloride, cross-linked vinylacetate-alcohol, etc. The container may be made of a mixture of resins of these materials, or a laminate composed of resin films of these materials. The container thus obtained is desired to be particularly resistant to high-pressure steam sterilization or hydrothermal sterilization.

The packaged container for containing the superficial cerebral vascular bleeding inhibitor of the present invention is produced by packaging the above gas-permeable plastic container with a gas-barrier packaging member, and establishing a carbon-dioxide-containing gas atmosphere in the space between the container and the packaging member.

The gas-barrier packaging member may be any of those typically used, and specific examples include polyethylene terephthalate (PET), ethylene vinylalcohol copolymer (EVOH), polyvinylidene chloride (PVDC), those having a vapor-deposition layer of silicon oxide or aluminum oxide on these materials, those consisting of multilayer films made from combinations of these materials, etc. The shape and size of these packaging members are not limited insofar as they are able to package the above plastic container, leaving enough space between the container and the packaging member to enclose a carbon dioxide-containing gas after packaging. The suitable volume of the above space is about 0.1 to about 0.8 times the volume of the solution in the container.

To establish a carbon dioxide-containing gas atmosphere in the space between the above container and the packaging member, the following method, for example, that encloses a carbon-dioxide-containing gas such as a mixed gas of carbon dioxide gas and air, a mixed gas of carbon dioxide gas and nitrogen gas, etc., in the above-described space can be employed. Alternatively employable is a method that encloses in the above space a carbon-dioxide-gas-generating oxygen absorber, which absorbs oxygen gas present in the space and releases carbon dioxide gas equal to the volume of oxygen gas absorbed. Examples of advantageously usable carbon-dioxide-gas-generating oxygen absorbers include "Ageless G" manufactured by Mitsubishi Gas Chemical Company, Inc. and "Keep Fresh Type C" manufactured by Toppan Printing Co., Ltd., etc.

By the employment of the above structure, the carbon dioxide gas present in the space between the container and the packaging member passes through the wall of the gas-permeable plastic container and is absorbed into Solution A, and the partial pressure of the carbon dioxide gas in Solution A equilibrates with the partial pressure of the carbon dioxide gas in the space, whereby the carbon dioxide gas acts as a pH-adjusting agent of Solution A.

The packaged container for containing the superficial cerebral vascular bleeding inhibitor of the present invention preferably may have, within the space between the container and the packaging member, a pH-indicating device (including those termed pinhole detectors) that detects the concentration of carbon dioxide in the space and undergoes a change in color in accordance with a change in the concentration of the carbon dioxide.

The pH-indicating device herein may be any of those that undergo a change in color in accordance with a change in the concentration of carbon dioxide in the above space. Examples include those containing a carbonate-containing solution and a pH indicator in a packet, etc. Specific examples thereof are as described in detail in, e.g., WO 97/48365, etc.

The pH indicator to be added to the above internal solution of the pH-indicating device may be selected from a variety of acid-base indicators capable of indicating a change in the pH of the internal solution of the device as a color change. In particular, a preferable example is a pH indicator that sensitively undergoes a change in color (discoloration) near a pH value of the above internal solution of the pH-indicating device at the equilibrium concentration of carbon dioxide in the space, wherein the aforementioned pH value corresponds to a pH value at which the effectiveness of a medical solution is impaired (i.e., the upper limit value according to Japanese Pharmacopoeia Standards for the product) by carbon dioxide gas released from the medical solution as a result of, for example, an accident such as a the formation of a pinhole in the packaging member. Generally, the pH at which the effectiveness as of a medical solution is impaired is on the alkaline side (e.g.; the standardized upper limit for a 7% aqueous solution of sodium bicarbonate is pH 8.6 according to Japanese Pharmacopoeia XIII, and the corresponding concentration of carbon dioxide is about 19%). Since the pH of the internal solution of the pH-indicating device, which is proportional to the pH of the bicarbonate ion-containing solution, is also, on the alkaline side (e.g., the pH of a 0.28% aqueous solution of sodium bicarbonate is 7.0), the pH-indicating agent described above is preferably a substance that undergoes a change in color on the weak alkaline side.

Particularly a preferable pH indicator has properties as follows; (1) a narrow color change area, (2) a high color intensity, (3) a suitable direction of color change (from indistinctive to distinctive colors), (4) outstanding hygienic properties (the substance itself is highly safe and not migratory), and (5) good stability with the initial color change property being sustained for an extended time. In the present invention, a pH indicator having these properties is desirably used. Preferable examples of a pH indicator include neutral red, aurin, phenol red, o-cresol red, α-naphtholphthalein, m-cresol purple, orange I, phenolphthalein, etc. Among these, phenol red (changes from yellow to red at pH 6.8 to 8.4 or higher), o-cresol red (changes from yellow to red at pH 7.2 to 8.8 or higher), and m-cresol purple (changes from yellow to purple at pH 7.6 to 9.2 or higher) are particularly suitable.

The concentration of the above pH indicator is not particularly limited insofar as a change in color is easy to visually observe. The concentration is preferably selected from a range of about 10 to about 2000 ppm, for example, depending on the size (thickness of the liquid layer) of the packet in which the pH indicator is enclosed together with the above internal indicating device solution.

The packet enclosing the above internal solution and the pH indicator can be produced by a known method. A material for the gas-permeable plastic container to be used for the packet may be those having gas-permeability (air-permeability) equal to or higher than that of materials for the container containing the above-described superficial cerebral vascular bleeding inhibitor. The above packet can be manufactured, for example, by a method in which forming, filling and sealing are continuously performed using a vertical 3-side sealer, a vertical pillow packaging machine, a rotary packer, and the like.

When the above manufacturing method is employed, the material for the packet is preferably a laminated film in view of machine processability. Particularly, when a polyethylene container is used as the container containing the bleeding inhibitor, a polypropylene (outer layer)-polyethylene (inner layer) laminate film or a poly-4-methyl-1-pentene (outer layer)-polyethylene (inner layer) laminate film are preferred.

Regarding the size of the packet and the volume of the internal solution, if the amount of the internal solution enclosed in the packet is too small, the thickness of the liquid layer in the indicating device will be too thin, whereby a visual determination of the color change is likely to be difficult. For this reason, the packet size and the internal solution volume should be suitably determined in consideration of the ease of determining the color change as well as the sizes of the packaging member and the container containing the bleeding inhibitor.

The pH-indicating device thus prepared may develop turbidity owing to bacterial growth in the internal solution during prolonged storage. To prevent or control this problem, it can be sterilized by high-pressure steam sterilization. Alternatively, an antiseptic such as benzalkonium chloride, chlorohexidine gluconate, etc., an antibacterial agent such as nalidixic acid, norfloxacin, etc., and/or a preservative such as p-hydroxybenzoic esters, benzyl alcohol, etc., may be added as necessary.

The packet is disposed in the space simply by packaging the container containing the bleeding inhibitor and the packet together with the packaging member. The position at which the packet is disposed is not limited insofar as the packet can be visually observed from outside even after being packaged with the packaging member. In this manner, an improved package can be obtained which allows a visual determination of a change in the pH of the superficial cerebral vascular bleeding inhibitor.

In the packaged container for containing the bleeding inhibitor having the above structure, an ink composition for detecting carbon dioxide, which contains a pH indicator, binder (thickener) and solvent may be used as a pH-indicating device. When such an ink composition is used to provide an indication member for detecting the concentration of carbon dioxide in the space between the container for containing the superficial cerebral vascular bleeding inhibitor and the packaging member, a visual determination of a change in the pH of the superficial cerebral vascular bleeding inhibitor is enabled as in the case of employing a pH-indicating device which contains a carbonate-containing solution and a pH indicator in a packet. The ink composition can be utilized as an indication member for detecting carbon dioxide by various methods. For example, a plastic film on which the ink composition is applied may be disposed in the space; the ink composition may be applied on the inner surface of the packaging member; the ink composition may be applied on the outer surface of the container containing the superficial cerebral vascular bleeding inhibitor, etc. Specific examples of such ink compositions for detecting carbon dioxide and the applications thereof are as described in detail in WO 01/44385, etc.

In the present invention, the procedures for filling the superficial cerebral vascular bleeding inhibitor into the container (each chamber in the container), sterilizing the fluid, packaging the container with the packaging member as well as establishing a carbon dioxide atmosphere within the space are the same as those typically employed for manufacturing injection solutions, and are hence easily carried out.

A preferable embodiment of the packaged container for containing the superficial cerebral vascular bleeding inhibitor of the present invention is as shown in an attached drawing (FIG. 1). The package comprises a gas-permeable plastic container 2 having two chambers partitioned by an intercommunicable sealing member 6, and a gas-barrier packaging member 3 enclosing the container, with a carbon dioxide atmosphere established in a space 4 between the container and the packaging member, and a pH-indicating device 5 disposed in the space 4. Each chamber of the above container 2 contains liquid solution 1, which will be the composition of the superficial cerebral vascular bleeding inhibitor of the present invention when admixed.

Having the above structure, the packaged product of the present invention can assure the following advantages: a product is not easily breakable, is adaptable for increased capacity, and has a reduced weight due to the use of a plastic container; problems such as the occurrence of precipitation and coloration are reliably avoided due to the container having two chambers; dissipation of carbon dioxide released from the superficial cerebral vascular bleeding inhibitor (a bicarbonate ion-containing solution) is prevented due to the employment of the gas-barrier packaging member and the establishment of a carbon dioxide atmosphere in the space; and consequent maintenance of the solution pH at a constant value is attained. Further, the packaged container containing the superficial cerebral vascular bleeding inhibitor of the present invention in which the pH-indicating device described earlier is disposed offers easy visual observation of the pH change and the degradation of the fluid caused by problems such as prolonged storage or formation of a pinhole in the packaging member. Furthermore, the packaged product of the present invention has the advantage of being easily manufactured by conventional techniques in any of the above embodiments.

Moreover, the superficial cerebral vascular bleeding inhibitor of the present invention may be stored in a medical solution container made of a material to which a gas-barrier property is imparted. Such a medical solution container made of a gas-barrier material may be a container formed of a multi-layered plastic film including a gas-barrier layer. Examples of medical solution containers having such a structure are those disclosed in Japanese Unexamined Patent Publications Nos. 2002-234102 and 05-8318, etc. An example of a usable container is a container formed of a multi-layered film wherein an inner layer is made of gas-permeable polyethylene film and an outer layer is made of polypropylene film with ethylene vinylalcohol copolymer (EVOH), i.e., a gas-barrier film, interposed therebetween. The gas-barrier film preferably used is a transparent film so as to enable the visual observation of the medical solution. The medical solution container to which the gas-barrier properties are imparted may be a container having at least two intercommunicable chambers.

Another embodiment of the gas-barrier medical solution container is a container having a structure in which both surfaces of a gas-permeable plastic film constituting the container are covered by gas-barrier films. In this embodiment, when the medical solution container made of the gas-permeable plastic film consists of two chambers, for example, only the chamber where a bicarbonate ion-containing solution (Solution A) is contained may be covered with a gas-barrier film. The barrier film is preferably a transparent film so that the medical solution can be visually observed. Examples of such medical solution containers are described in Japanese Unexamined Patent Publications Nos. 11-276547 and 2003-267451, Japanese Registered Utility Model No. 3112358, etc.

When the superficial cerebral vascular bleeding inhibitor of the present invention is stored in a gas-barrier medical solution container, the aforementioned ink composition for detecting carbon dioxide, which contains a pH indicator, binder (thickener)., and solvent, may be used to provide an indication member for detecting the concentration of carbon dioxide at an opening portion of the container body. For example, the container can have a structure wherein the opening portion of the container body is sealed using a gas-permeable sealer whose outside is detachably sealed by a gas-barrier covering member, and a gas detector is disposed between the covering, member and the gas-permeable sealer. Owing to this structure, when the sealing property of the medical solution container is impaired, it can be easily detected from outside. Specific examples of methods for disposing the gas detector include the following: a method wherein the above ink composition is applied to the inner surface of a gas-barrier covering member formed on the outside the gas-permeable sealer; a method wherein the ink composition is thus applied, followed by adhesion of a protective film thereon; and the like. Such a medical solution container provided, at the opening portion thereof, with an indication member for detecting the concentration of carbon dioxide is described in, e.g., Japanese Unexamined Patent Publication No. 2005-349182.

(3) Application of the Superficial Cerebral Vascular Bleeding Inhibitor of the Present Invention The superficial cerebral vascular bleeding inhibitor of the present invention can be used in a method of irrigating or perfusing the inside of the cranium or cerebrospinal cavity during intracranial surgery. For example, the bleeding inhibitor of the present invention contained in the gas-permeable plastic container having at least two intercommunicable chambers can be practically used after the above two chambers are brought into intercommunication to admix (or dilute) the internal solutions of both chambers.

As specific examples, the superficial cerebral vascular bleeding inhibitor of the present invention can be used in a method for irrigating the operating field during neurosurgery (trepanation, craniotomy). It can also be used as a perfusion fluid in neuroendoscopic surgery, and the like. When the superficial cerebral vascular bleeding inhibitor of the present invention is used in the above-described manner, bleeding from superficial cerebral blood vessels can be significantly inhibited or prevented, compared with the case where, for example, physiological saline solution or the like is used for irrigation or perfusion.

The amount of the superficial cerebral vascular bleeding inhibitor of the present invention that is used is not particularly limited, and can be suitably determined in accordance with the purpose of use in surgeries mentioned above. It is typically used at a maximum amount of about 4000 mL as a guide, and the amount can be increased based on the judgment of a doctor during actual surgery. Usages of the bleeding inhibitor may be suitably varied depending on the form of surgery. For example, the bleeding inhibitor may be suitably used in the following manners: the inhibitor is directly dropped into the operating field using a dropper or syringe; the fluid is sprayed (insufflated) to necessary areas such as the operating field; the inhibitor is drained (perfused) at a constant rate to necessary areas such as the operating field using a suitable tube or the like; a gauze or the like impregnated with the inhibitor is placed on the brain surface to prevent the surface from drying; the fluid is dropped from instruments such as a coagulator and drill when using these instruments; etc.

Advantageous Effects of Invention

The superficial cerebral vascular bleeding inhibitor of the present invention can effectively prevent or inhibit bleeding from superficial cerebral blood vessels in the field of neurosurgery such as intracranial surgery. As a result, a clear operating field can be secured during intracranial surgery and the occurrence of post-surgery damage can be inhibited.

BRIEF DESCRIPTION OF DRAWINGS

FIG. 1 is a schematic view showing a preferred embodiment of a packaged container for containing a superficial cerebral vascular bleeding inhibitor of the present invention.

REFERENCE SIGNS LIST

1 Superficial cerebral vascular bleeding inhibitor of the present invention
2 Gas-permeable plastic multiple-chamber container
3 Gas-barrier packaging member
4 Space between the gas-permeable plastic multiple-chamber container 2 and gas-barrier packaging member 3
5 pH-indicating device
6 Intercommunicable seal portion Description of Embodiment The present invention is described in further detail below in reference to Examples, but is not limited thereto.

Example 1

Each component listed in Tables 1 to 6 below was dissolved in distilled water for injection to prepare bleeding inhibitors 1 to 6 of the present invention.

TABLE 1

Bleeding inhibitor 1 of the present invention

| Components (per 500 mL) | Amount (g) |
| --- | --- |
| Sodium chloride | 4.5 |
| Potassium chloride | 0.104 |
| Calcium chloride | 0.064 |

TABLE 2

Bleeding inhibitor 2 of the present invention

| Components (per 500 mL) | Amount (g) |
| --- | --- |
| Sodium chloride | 4.5 |
| Potassium chloride | 0.15 |
| Calcium chloride | 0.08 |

TABLE 3

Bleeding inhibitor 3 of the present invention

| Components (per 500 mL) | Amount (g) |
| --- | --- |
| Sodium chloride | 3.0 |
| Potassium chloride | 0.15 |
| Calcium chloride | 0.1 |
| Sodium lactate | 1.55 |

TABLE 4

Bleeding inhibitor 4 of the present invention

| Components (per 500 mL) | Amount (g) |
| --- | --- |
| Sodium chloride | 3.185 |
| Potassium chloride | 0.149 |
| Calcium gluconate | 0.337 |
| Magnesium chloride | 0.102 |
| Anhydrous sodium acetate | 1.025 |
| Sodium citrate | 0.294 |
| Glucose | 5.000 |

TABLE 5

Bleeding inhibitor 5 of the present invention

| Components | Amount (g) |
| --- | --- |
| Upper Chamber Solution (per 150 mL) | |
| Sodium chloride | 1.200 |
| Calcium chloride • dihydrate | 0.085 |
| Magnesium chloride • hexahydrate | 0.110 |
| Glucose | 0.305 |
| Lower Chamber Solution (per 350 mL) | |
| Sodium bicarbonate | 0.970 |
| Potassium dihydrogenphosphate | 0.075 |

TABLE 5-continued

Bleeding inhibitor 5 of the present invention

| Components | Amount (g) |
|---|---|
| Sodium chloride | 2.375 |
| Potassium chloride | 0.065 |

TABLE 6

Bleeding inhibitor 6 of the present invention

| Components (per 500 mL) | Amount (g) |
|---|---|
| Sodium chloride | 4.5 |
| Potassium chloride | 0.064 |

Note that the bleeding inhibitors 1 to 4 and 6 of the present invention were prepared to be treated as one-component bleeding inhibitors by dissolving all the components listed in each table in distilled water for injection.

As for the bleeding inhibitor 5 of the present invention, each component, shown under the titles Upper Chamber Solution and Lower Chamber Solution in Table 5 above, was weighed, and mixed and dissolved in distilled water for injection, thereby preparing 150 mL of upper chamber solution and 350 mL of lower chamber solution. The lower chamber solution thus obtained was charged through a solution outlet into the lower chamber (a chamber equipped with the solution outlet connecting to a port portion, illustrated in the upper part of FIG. 1) of a container 2 (made of polyethylene), of the packaged container for containing the superficial cerebral vascular bleeding inhibitor as shown in FIG. 1, and the outlet was tightly sealed. Similarly, the obtained upper chamber solution was charged into the upper chamber (a chamber separated from the above lower chamber by a partitioning wall, the chamber adjoining to a suspension portion, illustrated in the lower part of the figure) before the upper chamber was tightly sealed, and thereafter the upper chamber was hermetically sealed. Then, the obtained container was subjected to high-pressure steam sterilization, dehydrated, and packaged in a gas-barrier film (Bovlon Film, product of Nippon Synthetic Chemical Industry Co., Ltd., a biaxially oriented polyvinyl alcohol film, thickness: 14 μm), together with a pH-indicating device (the device disclosed in Production Example 5 of Japanese Unexamined Patent Publication No. 11-197215). When packaging was performed, about 400 ml of a mixed gas of 18% carbon dioxide and air was filled into the space between the container and the packaging member. A packaged container containing the superficial cerebral vascular bleeding inhibitor, i.e., a packaged container containing the bleeding inhibitor 5 of the present invention, was thus obtained.

Tables 7 to 12 below show the electrolyte ion concentration and the concentration of other components in the bleeding inhibitors 1 to 6 of the present invention. As for the bleeding inhibitor 5 of the present invention, the table shows the concentration of the mixed solution obtained by mixing the upper chamber solution and the lower chamber solution.

TABLE 7

Bleeding inhibitor 1 of the present invention

| $Na^+$ | 154 mEq/L |
|---|---|
| $K^+$ | 2.8 mEq/L |

TABLE 7-continued

Bleeding inhibitor 1 of the present invention

| $Ca^{2+}$ | 2.3 mEq/L |
|---|---|
| $Cl^-$ | 159 mEq/L |

TABLE 8

Bleeding inhibitor 2 of the present invention

| $Na^+$ | 154 mEq/L |
|---|---|
| $K^+$ | 4 mEq/L |
| $Ca^{2+}$ | 3 mEq/L |
| $Cl^-$ | 161 mEq/L |

TABLE 9

Bleeding inhibitor 3 of the present invention

| $Na^+$ | 130 mEq/L |
|---|---|
| $K^+$ | 4 mEq/L |
| $Ca^{2+}$ | 3 mEq/L |
| $Cl^-$ | 109 mEq/L |
| Lactate ion$^-$ | 28 mEq/L |

TABLE 10

Bleeding inhibitor 4 of the present invention

| $Na^+$ | 140 mEq/L |
|---|---|
| $K^+$ | 4 mEq/L |
| $Ca^{2+}$ | 3 mEq/L |
| $Mg^{2+}$ | 2 mEq/L |
| $Cl^-$ | 115 mEq/L |
| Acetate ion$^-$ | 28 mEq/L |
| Gluconate ion$^-$ | 3 mEq/L |
| Citrate ion$^{3-}$ | 6 mEq/L |

TABLE 11

Bleeding inhibitor 5 of the present invention

| $Na^+$ | 145.4 mEq/L |
|---|---|
| $K^+$ | 2.8 mEq/L |
| $Mg^{2+}$ | 2.2 mEq/L |
| $Ca^{2+}$ | 2.3 mEq/L |
| $Cl^-$ | 128.5 mEq/L |
| $HCO_3^-$ | 23.1 mEq/L |
| Pi (Phosphoric) | 1.1 mmol/L |
| Glucose | 0.61 g/L |

TABLE 12

Bleeding inhibitor 6 of the present invention

| $Na^+$ | 154 mEq/L |
|---|---|
| $Ca^{2+}$ | 2.3 mEq/L |
| $Cl^-$ | 156 mEq/L |

Test Example 1

The bleeding-inhibiting effect in superficial cerebral irrigation was studied using the mouse model according to the following method.

First, a mouse was anesthetized with urethane, and fixed to a brain stereotaxic apparatus. The body temperature of the mouse was maintained at 37° C. by a feedback device for maintaining body temperature. A bone window was created on the left parietal bone using a drill, and then the dura mater and arachnoid mater were removed. Superficial cerebral blood vessels were cut by this procedure, creating many cuts on the brain surface.

This brain surface was perfused for 10 minutes (discharge rate: 100 mL/hr) using physiological saline solution ("Otsuka Normal Saline" ($Na^+$ 154 mEq/L and $Cl^-$ 154 mEq/L) manufactured by Otsuka Pharmaceutical Factory, Inc.), and the number of bleeding spots per operating field was counted under a stereomicroscope.

Subsequently, the perfusion fluid was replaced with the bleeding inhibitor 1, 2, 3, or 5 of the present invention, and the perfusion was performed for a second-time in the same manner for 10 minutes. Then, the number of bleeding spots per operating field was counted. Note that, as a comparison, the second perfusion was performed in the same manner but using physiological saline solution (physiological saline solution with added potassium) to which potassium chloride was added in the amount of 0.104 g per 500 mL (the concentration after mixing: 2.8 mEq/L), and the number of bleeding spots per operating field was counted under a stereomicroscope.

Table 13 below shows the results of the bleeding spots counted according to the above method.

TABLE 13

| After the first perfusion | | After the second perfusion | |
|---|---|---|---|
| Perfusion fluid | Number of bleeding spots | Perfusion fluid | Number of bleeding spots |
| Physiological saline solution | 11 | Bleeding inhibitor 1 of the present invention | 6 |
| Physiological saline solution | 6 | Bleeding inhibitor 2 of the present invention | 0 |
| Physiological saline solution | 4 | Bleeding inhibitor 3 of the present invention | 0 |
| Physiological saline solution | 4 | Bleeding inhibitor 5 of the present invention | 0 |
| Physiological saline solution | 7 | Physiological saline solution with added potassium | 7 |

As is clear from the above results, although many bleeding spots on the brain surface were counted when perfusion was performed using physiological saline solution, the number of bleeding spots was reduced to approximately half when perfusion was performed using the bleeding inhibitor 1 of the present invention, and no bleeding was found when the bleeding inhibitors 2, 3, and 5 of the present invention were used for the perfusion. Note that no bleeding-inhibiting effect was observed when the second perfusion was performed using physiological saline solution with added potassium.

Test Example 2

The bleeding-inhibiting effect in superficial cerebral irrigation was studied using the mouse model in the same manner as in Test Example 1 except that the first perfusion and the second perfusion were performed using the bleeding inhibitors shown in Table 12 below.

Table 14 below shows the results of the bleeding spots counted according to the above method.

TABLE 14

| After the first perfusion | | After the second perfusion | |
|---|---|---|---|
| Perfusion fluid | Number of bleeding spots | Perfusion fluid | Number of bleeding spots |
| Bleeding inhibitor 3 of the present invention | 0 | Bleeding inhibitor 5 of the present invention | 0 |
| Bleeding inhibitor 5 of the present invention | 0 | Bleeding inhibitor 3 of the present invention | 0 |
| Bleeding inhibitor 4 of the present invention | 0 | Bleeding inhibitor 5 of the present invention | 0 |
| Bleeding inhibitor 5 of the present invention | 1 | Bleeding inhibitor 4 of the present invention | 1 |

As is clear from the above results, the lactate ion-containing bleeding inhibitor 3 of the present invention, the acetate ion-containing bleeding inhibitor 4 of the present invention, and the carbonate ion-containing bleeding inhibitor 5 of the present invention all exhibited a superior bleeding-inhibiting effect.

Test Example 3

The bleeding-inhibiting effect in superficial cerebral irrigation was studied using 6 mice for each study group by the same method as in Test Example 1.

The test substances were the bleeding inhibitor 3 of the present invention, the bleeding inhibitor 5 of the present invention, and physiological saline solution ("Otsuka Normal Saline" ($Na^+$ 154 mEq/L and $Cl^-$ 154 mEq/L) manufactured by Otsuka Pharmaceutical Factory, Inc.).

Table 15 below shows the results of the bleeding spots counted according to the above method. The results shown are average values and standard deviations.

TABLE 15

| After the first perfusion | | After the second perfusion | |
|---|---|---|---|
| Perfusion fluid | Number of bleeding spots (average ± SD) (n = 6) | Perfusion fluid | Number of bleeding spots (average ± SD) (n = 6) |
| Bleeding inhibitor 5 of the present invention | 2.8 ± 1.7 | Physiological saline solution | 5.2 ± 2.2 |
| Physiological saline solution | 15.7 ± 3.4 | Bleeding inhibitor 5 of the present invention | 3.0 ± 2.8 |
| Bleeding inhibitor 5 of the present invention | 3.2 ± 2.4 | Bleeding inhibitor 3 of the present invention | 2.0 ± 1.3 |
| Bleeding inhibitor 3 of the present invention | 2.7 ± 1.6 | Bleeding inhibitor 5 of the present invention | 1.5 ± 2.0 |

As is clear from the above results, the bleeding inhibitors 3 and 5 of the present invention both exhibited a superior bleeding-inhibiting effect.

Test Example 4

The bleeding-inhibiting effect in superficial cerebral irrigation was studied using the mouse model according to the following method.

The test substances were the bleeding inhibitor 1 of the present invention, the bleeding inhibitor 6 of the present invention, physiological saline solution ("Otsuka Normal Saline" ($Na^+$ 154 mEq/L and $Cl^-$ 154 mEq/L) manufactured by Otsuka Pharmaceutical Factory, Inc.), and physiological saline solution (physiological saline solution with added potassium) to which potassium chloride was added in the amount of 0.104 g per 500 mL (the concentration after mixing: 2.8 mEq/L).

First, a mouse was anesthetized with urethane, and fixed to a brain stereotaxic apparatus. The body temperature of the mouse was maintained at 37° C. by a feedback device for maintaining body temperature. Six mice were used for each study group.

Then, a bone window was created on the left parietal bone of each mouse using a drill, and the dura mater and arachnoid mater were removed by irrigating using the test substances at an irrigation rate of 150 mL/hr. Superficial cerebral blood vessels were cut by this procedure, creating many cuts on the brain surface.

After the bone window was created, the irrigation rate was changed to 100 mL/hr and perfusion was performed for 10 minutes. Then, the number of bleeding spots per operating field was counted under a stereomicroscope.

Table 16 below shows the results of the bleeding spots counted according to the above method. The results shown are average values and standard deviations.

TABLE 16

| Test substance | Bleeding inhibitor 1 of the present invention | Bleeding inhibitor 6 of the present invention | Physiological saline solution with added potassium | Physiological saline solution |
|---|---|---|---|---|
| Number of bleeding spots (average ± SD) (n = 6) | 2.2 ± 1.5 | 4.3 ± 1.6 | 13.5 ± 3.9 | 14.0 ± 2.8 |

As is clear from the above results, the bleeding inhibitors 1 and 6 of the present invention both exhibited a superior bleeding—inhibiting effect, compared with physiological saline solutions, one with added potassium and one without. In particular, the bleeding inhibitor 1 of the present invention containing both potassium ion and calcium ion exhibited an excellent bleeding-inhibiting effect.

The invention claimed is:

1. A method for inhibiting bleeding from superficial cerebral blood vessels to secure clear vision of an operating field during intracranial surgery, the method comprising:
    mixing a first aqueous solution comprising calcium ion and a second aqueous solution comprising bicarbonate ion to form a superficial cerebral vascular bleeding inhibitor at a time of irrigating or perfusing said operating field with said superficial cerebral vascular bleeding inhibitor during said intracranial surgery, wherein said intracranial surgery is a craniotomy procedure or a neuroendoscopic operation, and
    irrigating or perfusing said operating field with said superficial cerebral vascular bleeding inhibitor during said intracranial surgery,
    wherein at least one of said first aqueous solution and said second aqueous solution further comprises sodium ion and chloride ion,
    wherein said superficial cerebral vascular bleeding inhibitor comprises:
    120 to 160 mEq/L of sodium ion,
    2.0 to 3.5 mEq/L of calcium ion,
    75 to 165 mEq/L of chloride ion, and
    2.5 to 4.5 mEq/L of potassium ion,
    wherein said irrigating or perfusing with said superficial cerebral vascular bleeding inhibitor inhibits bleeding from said superficial cerebral blood vessels to secure clear vision of said operating field during said intracanial surgery.

2. The method for inhibiting bleeding from superficial cerebral blood vessels to secure clear vision of an operating field during intracranial surgery according to claim 1,
    wherein at least one of said first aqueous solution and said second aqueous solution further comprises at least one ion selected from the group consisting of lactate ion and acetate ion, and
    wherein a total concentration of bicarbonate ion and said at least one ion selected from the group consisting of lactate ion and acetate ion in said superficial cerebral vascular bleeding inhibitor is 5 to 45 mEq/L.

* * * * *